United States Patent
Pennell

(10) Patent No.: US 10,197,171 B2
(45) Date of Patent: Feb. 5, 2019

(54) METHOD AND APPARATUS FOR DRAINING

(71) Applicant: Infinivation Biomedical LLC, Moravia, NY (US)

(72) Inventor: Thomas J. Pennell, Moravia, NY (US)

(73) Assignee: Infinivation Biomedical LLC, Moravia, NY (US)

( * ) Notice: Subject to any disclaimer, the term of this patent is extended or adjusted under 35 U.S.C. 154(b) by 279 days.

(21) Appl. No.: 15/130,187

(22) Filed: Apr. 15, 2016

(65) Prior Publication Data

US 2017/0296796 A1 Oct. 19, 2017

(51) Int. Cl.
*A61M 1/00* (2006.01)
*F16K 15/02* (2006.01)
*A61M 39/24* (2006.01)
*A61M 27/00* (2006.01)
*A61M 39/22* (2006.01)

(52) U.S. Cl.
CPC ......... *F16K 15/026* (2013.01); *A61M 27/006* (2013.01); *A61M 39/24* (2013.01); *A61M 1/0019* (2013.01); *A61M 2027/004* (2013.01); *A61M 2039/226* (2013.01); *A61M 2039/2493* (2013.01); *A61M 2202/0464* (2013.01)

(58) Field of Classification Search
CPC .......... A61M 1/0019; A61M 2027/004; A61M 2039/226; A61M 2039/2493; A61M 2202/0464; A61M 27/006; A61M 39/24
See application file for complete search history.

(56) References Cited

U.S. PATENT DOCUMENTS

2012/0232461 A1* 9/2012 Seaver ............... A61M 27/006 604/9
2015/0112289 A1* 4/2015 Stebbins ............. A61M 1/0021 604/318

* cited by examiner

*Primary Examiner* — Tatyana Zalukaeva
*Assistant Examiner* — Kai Weng
(74) *Attorney, Agent, or Firm* — Timothy W. Menasco, Esq.; Harter Secrest & Emery LLP

(57) ABSTRACT

The present disclosure provides a method and apparatus for draining. The apparatus includes a body, the body having a first compartment adjacent to a second compartment, the first compartment having an inlet port fluidly connected to an outlet port, the inlet port defining a needle seat within the first compartment, a first rod hole for operation with a second rod hole in the second compartment, and a plurality of venting holes, the second compartment having a plurality of spaced notches along. The apparatus further includes a setting rod, the setting rod having a shaft and a sealing head, the shaft sized to be slideably maintained in the first rod hole and the second rod hole, the sealing head slideably attached to an end of the shaft and sized to obstruct fluid flow from the inlet port at the needle seat.

17 Claims, 6 Drawing Sheets

METHOD AND APPARATUS FOR DRAINING

BACKGROUND OF THE DISCLOSURE

Field of the Disclosure

Exemplary embodiments of the present disclosure relate to a method and apparatus for draining. The present disclosure relates more particularly to a method and apparatus for draining body fluid.

Description of Related Art

Any injury that results in trauma to the skull or brain can be classified as a head injury. This can include neuronal injuries, hemorrhages, vascular injuries, cranial nerve injuries, and subdural hygromas. Some head injuries are benign in nature and require no treatment beyond analgesics and close monitoring for potential complication such as intracranial bleeding. However, if the brain has been severely damaged by trauma or other means, neurosurgical evaluation may be required. Treatments for the injury can include controlling elevated intracranial pressure through cerebrospinal fluid diversion.

An external ventricular drain (EVD), also known as an extraventricular drain or ventriculostomy, is a device used in neurosurgery that relieves elevated intracranial pressure and hydrocephalus due to cerebrospinal fluid or other excess fluid around the brain. An EVD is typically placed in a patient by neurosurgeons and managed by Intensive Care Unit (ICU) nurses and critical care staff to drain fluid from the ventricles of the brain as well as to monitor intracranial pressure.

Usually, an EVD is used to monitor pressure in patients with brain injuries, intracranial bleeds or other brain abnormalities that lead to increased fluid build-up. In addition to draining fluid build-up, an EVD will also sometimes remove blood from the ventricular spaces. This can be beneficial because blood is an irritant to brain tissue, which can cause complications to a patient in recovery and can contribute to increased intracranial pressure.

BRIEF SUMMARY OF THE DISCLOSURE

In view of the foregoing, it is an object of the present disclosure to provide a method and apparatus for draining.

A first exemplary embodiment of the present disclosure provides an apparatus for draining. The apparatus includes a body, the body having a first compartment adjacent to a second compartment, the first compartment having an inlet port fluidly connected to an outlet port, the inlet port defining a needle seat within the first compartment, a first rod hole for operation with a second rod hole in the second compartment, and a plurality of venting holes, the second compartment having a plurality of spaced notches along. The apparatus further includes a setting rod, the setting rod having a shaft and a sealing head, the shaft sized to be slideably maintained in the first rod hole and the second rod hole, the sealing head slideably attached to an end of the shaft and sized to obstruct fluid flow from the inlet port at the needle seat, and a bias member, the bias member intermediate the setting rod and the sealing head for exerting a force on the sealing head against the needle seat.

A second exemplary embodiment of the present disclosure provides a method for draining. The method includes providing a valve, the valve having a body, a setting rod having a shaft engageably connected to a bias member and a sealing head, the body having an inlet port fluidly connected to an outlet port, the inlet port defining a needle seat within the body, the sealing head moveably obstructing a flow of fluid up to a threshold pressure through the inlet port at the needle seat. The method further includes connecting the valve to a ventricle of a patient, wherein the valve is located in proximity to the ventricle such that an atmospheric pressure on the ventricle is substantially similar to the atmospheric pressure on the valve, and draining, through the valve, fluid from the ventricle.

A third exemplary embodiment of the present disclosure provides an apparatus for draining. The apparatus includes a valve body having valve chamber with a plurality of spaced apart stops, the valve chamber having an inlet port and an outlet port, the inlet port defining a valve seat, and a sealing head having a sealing surface moveable relative to the valve seat. The apparatus further includes a setting rod moveably connected to the valve body to a plurality of positions corresponding to the plurality of spaced apart stops, and a bias member interconnecting the setting rod and the sealing surface, wherein the bias member exerts a force on the sealing surface against the valve seat, the force on the sealing surface against the valve seat corresponding to the position of the setting rod.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

BRIEF DESCRIPTION OF THE SEVERAL VIEWS OF THE DRAWING(S)

DETAILED DESCRIPTION OF THE DISCLOSURE

Figure 1:
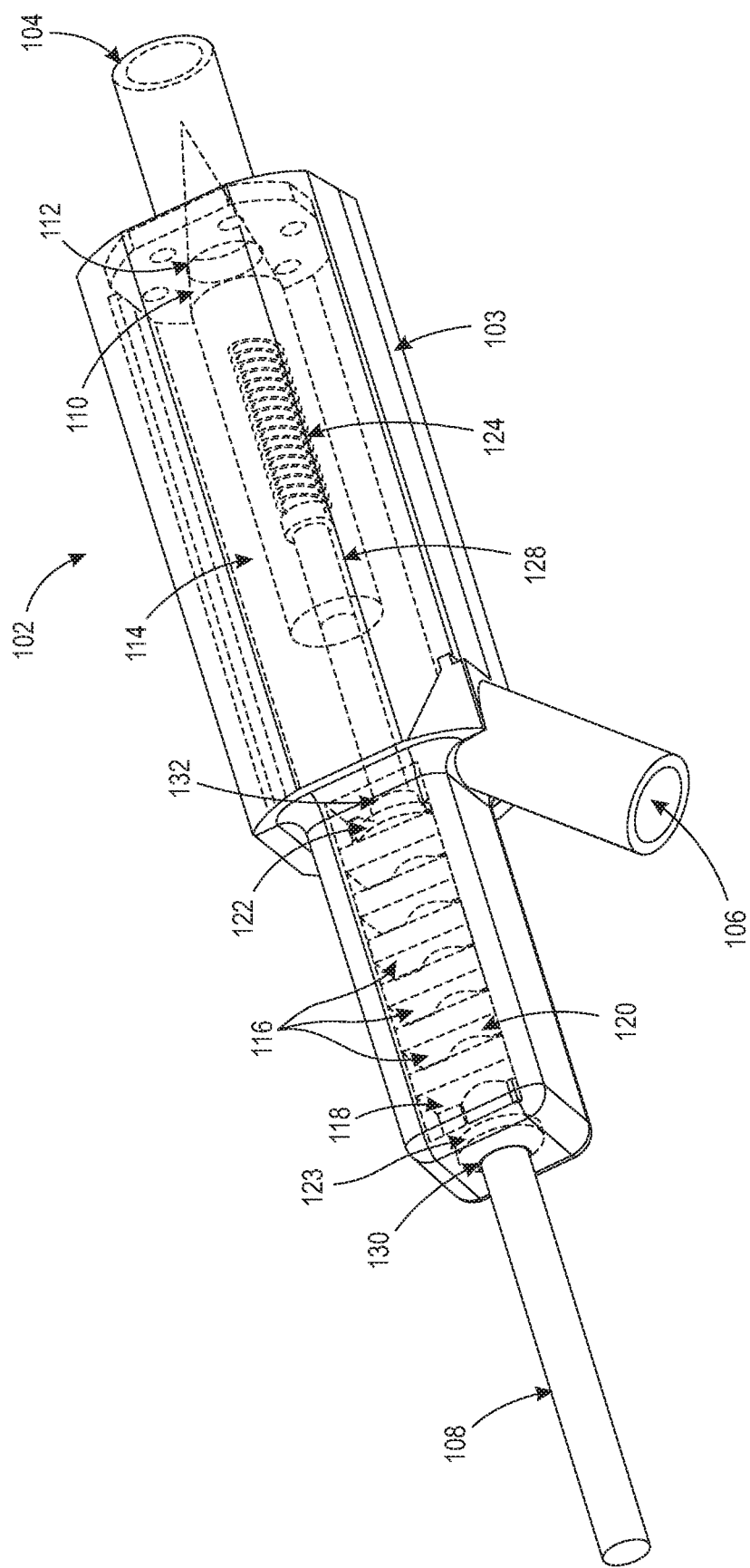
FIG. 1 is an exemplary valve suitable for use in practicing exemplary embodiments of this disclosure.

External ventricular drainage is a technique utilized by physicians in order to enable therapeutic drainage of cerebrospinal fluid (CSF) from the ventricles of the brain in order to relieve excess pressure within the cranium. External ventricular drainage is standard for monitoring of intracranial pressure (ICP).

Current EVD systems allow for successful drainage of cerebrospinal fluid under specific conditions. However, there are several drawbacks associated with current EVD systems. First, current EVD systems require nearly constant monitoring by medical professionals. Current systems require the patient or user to maintain their ventricles at the same horizontal level with the zero level of the EVD. In the event that a patient changes the vertical position of their ventricles relative to the zero level of the EVD, the EVD must be releveled by qualified clinical staff.

Two problems can occur if a patient is left unmonitored by healthcare professionals. Over drainage can occur if the patient's ventricles are above the zero level of the EVD. This can lead to ventricular collapse, and significant injury to the patient. Conversely, underdrainage can occur if the patient's ventricles are below the zero level of the EVD. This can lead to excessive intracranial pressure, leading to significant patient injury. Additionally, retrograde flow of air can occur into the cerebral ventricles causing further damage, and putting the patient at significant risk for infection.

Second, existing EVD systems are not conducive to patient rehabilitation. Early mobilization of a patient is key in minimizing patient recovery time, and improving overall patient outcome. Current EVD systems mount to an IV pole that must be wheeled alongside the patient when the patient is mobile. This system inhibits mobility of the patient and presents a tripping hazard. The EVD must also be closed to drainage while the patient is out of bed in order to prevent overdrainage due to the system not being level with the ventricles. This system limits the amount of time a patient can spend out of bed and mobilized.

Third, existing EVD systems are typically not MRI compatible because they are mounted an IV pole. This means that the drainage from the EVD would have to be discontinued for the duration of an MRI. This limits the amount of time the patient can spend in the MRI, putting the patient at risk of increased intracranial pressure due to lack of drainage.

Embodiments of the present disclosure can regulate the pressure of spinal fluid in a user's or patient's cerebral ventricles. Embodiments present a wearable valve design that greatly reduces the size of an EVD's pressure regulation component by regulating pressure through the compression of a spring rather than the relative height of a graduated cylinder.

Embodiments of the present disclosure provide a system that attaches a pressure regulation valve and other components (e.g., tubes, a fluid measuring device, and a drainage bag) to the patient's body and/or clothing. Aspects include a valve with pressure regulation capabilities wherein the pressure can be regulated by balancing hydrostatic pressure and spring force. The equation for hydrostatic pressure is:

Pressure=fluid density*gravity*height ($P=\rho g h$)

Embodiments of the present disclosure provide that the zero level of the EVD is intended to be leveled with the patient's ventricles. In other words, embodiments of the present EVD require embodiments of the present valve to be level with a patient's ventricles. Embodiments also provide an outlet of the fluid from the valve into a graduated cylinder at atmospheric pressure, thus the graduated cylinder will contain an atmospheric vent.

Embodiments of an exemplary valve will have a constant inlet area and will be able to incrementally control the drainage pressure, such as through use of a spring mechanism. An exemplary valve includes a needle (which includes a sealing head that interacts with a seat) and a seat, wherein the needle is in movable contact with the seat. The needle/seat interface is aided in its sealing ability by a soft coating (e.g., a silicone coating) allowing the surfaces to deform, leading to a fluid tight seal. This sealing surface can be applied to either the needle or the seat or both. A spring can be held within the needle in a central bore beginning at the opposing end of the needle from the sealing surface.

Embodiments of a graduated cylinder include a stopcock located at the base of the graduated cylinder allowing for periodic measurement of CSF and emptying of the graduated cylinder to a larger downstream collection reservoir (drainage bag).

In aspects of the disclosure, the pressure used to regulate drainage from the cerebral ventricles is based on spring pressure. The equation for spring force is:

Force=spring constant*compression distance ($F=kx$)

The pressure coming from the brain is equal to:

Force/area ($P=F/A$)

Embodiments of the present EVD can also be mounted on a standard IV pole configuration with the valve being aligned to the patient's ventricles. Thus, embodiments of the present EVD can be used in multiple configurations along with the overall construction having reduced size. Embodiments of the present EVD are configured with fasteners to make components easily detachable from the body so it can be removed in case of the patient requiring CPR compressions or other patient interaction.

In practice, embodiments of the EVD valve should be mounted at the level of the lateral cerebral ventricles at the site of the Foramen of Munro external to the scalp of the patient. Embodiments of the valve include an atmospheric vent at the level of the needle seat in order to properly regulate the outflow of CSF.

In one embodiment, a hydrophilic coating may be added to the tubing following the exit of the atmospherically vented valve and preceding the entrance of the atmospherically vented drip chamber to facilitate valve outflow.

Referring to FIG. 1, shown is an exemplary valve suitable for use in practicing exemplary embodiments of this disclosure. Depicted in FIG. 1 is valve 102. Embodiments of valve 102 are operable for regulating pressure of spinal fluid. Valve 102 includes body 103 and shaft 108. Body 103 includes an inlet port 104, outlet port 106, needle seat 112, flow cavity 114, grooves 116, shaft cavity 118, and o-rings 122, 123. Shaft 108 includes needle head 110, pin 120, and spring 124.

Inlet port 104 provides a passage to flow cavity 114. Inlet port 104 is fluidly connected through flow cavity 114 to outlet port 106. Inlet port 104 is operable for connecting with a flow tube and/or a ventricular catheter.

Outlet port 106 provides a passage from flow cavity 114. Outlet port 106 is operable for connecting with a flow tube and/or drip chamber and allows a flow of fluid from flow cavity 114 out through outlet port 106.

Embodiments of outlet port 106 provide that outlet port 106 is at 45 degree angle relative to the axis of inlet port 104. This configuration allows for fluid to flow towards outlet port 106 when body 103 is in either a horizontal and vertical position.

Flow cavity 114 fluidly connects inlet port 104 and outlet port 106. Flow cavity 114 provides an open cavity that allows a flow of a fluid. Flow cavity 114 encompasses a portion of shaft 108, which controls a flow through inlet port 104. Shaft 108 includes a needle head 110 and spring 124, which is moveable and bias against needle head 110. Needle head 110 with spring 124 operably press against needle seat 112 thereby obstructing a flow through inlet port 104 into flow cavity 114. Thus, shaft 108 with needle head 110 and spring 124 maintain a predetermined cracking pressure against needle seat 112.

Embodiments of needle head 110 can be coated in polydimethyl siloxane (PDMS) or another similar material in order to provide a soft sealing surface to allow for improved sealing of needle head 110 to the needle seat 112. A similar coating could also be applied to the needle seat 112 to accomplish the same. That is, the sealing surface is slightly compressible and resilient. The coating on needle head 110 or seat 112 may require an adhesion promoter in order to prevent silicone delamination after exposure to fluids.

The surface finish of both the needle head 110 and needle seat 112 is critical in order to maintain a proper seal. Improper sealing can lead to pre-leakage (flow through the valve prior to reaching its set pressure) or retrograde flow (air traveling past the valve seat toward the patient). The compressible resilient nature of the sealing surface accommodates manufacturing deviations in the needle head 110.

Shaft 108 extends through flow cavity 114, shaft cavity 118, and outside shaft cavity 118. Shaft 108 includes pin 120, which extends perpendicular from the long axis of shaft 108 within shaft cavity 118. Shaft 108 is moveable relative to body 103 such that shaft 108 can move in and out of body 103 longitudinally along its long axis. Additionally, shaft 108 can rotate about its long axis thereby changing the orientation of pin 120 relative to shaft cavity 118 and grooves 116. Shaft 108 can be rotated and moved longitudinally by a user through the portion of shaft 108 that extends outside of body 103.

Grooves 116 provide a series or plurality of grooves, or corresponding stops within shaft cavity 118 for removeably retaining pin 120 and shaft 108 relative to body 103. Shaft 108 is operable to slideably move through its long axis such that pin 120 can move closer to inlet port 104 and farther away from inlet port 104. Shaft 108 is also operable to rotate about its longitudinal axis such that pin 120 can move into and out of grooves 116 thereby locking or maintaining the position of shaft 108 relative to body 103. Grooves 116 also include a channel 126 that allows movement of shaft 108 with pin 120 through the long axis of channel 126. Each groove 116 with shaft 108, and pin 120 correspond to a predetermined cracking pressure between needle head 110 and needle seat 112 based on a compression of spring 124. In one embodiment, grooves 116 are spaced such that each incremental groove 116 corresponds to an increase or decrease of 2.5 mmHg. In one configuration, opposing series of grooves are used wherein the differences in cracking pressure between each groove within a series is 5 mmHg, and the opposing series are offset so that collectively the offset series provide for 2.5 mmHg increments. It should be appreciated that embodiments of grooves 116 can be in any arrangement that provide a means for shaft 108 to incrementally increase or decrease the cracking pressure against needle seat 112.

Spring 124 is operable to regulate pressure between needle head 110 and needle seat 112 in the range of 0-30 mmHg. It should be appreciated that embodiments of the present disclosure can be altered so as to accommodate different ranges of pressure regulation. Spring 124 and all valve components should be constructed of MRI compatible material (i.e., materials that are non-magnetic, and cause negligible heating, migration or image artifact in an MRI system). Embodiments of shaft 108 needle head 110 are designed to apply a specific amount of preload to the spring based on their weight.

O-rings 122, 123 and shaft 108 operably seal holes 130 and 132 in order to prevent leakage of CSF out of the valve 102. O-ring 123 seals is typically located at the distal end of the locking channel array. This o-ring can be made such that the o-ring incorporates a sheath which covers the advancement rod. This is used to prevent bacteria transferred to the rod from the person adjusting the valve from passing to the interior of the valve, and into the patient. This sheath should allow the rod to be advanced and retracted freely, and should be puncture/abrasion resistant. A suitable material for this may be a urethane or other flexible material.

O-rings 122, 123 are located within shaft cavity 118 at the inside surface of shaft cavity 118 at holes 130 and 132. Hole 130 provides a passage for shaft 108 to enter shaft cavity 118. Hole 132 provides a passage connecting shaft cavity 118 and flow cavity 114. O-rings 122 maintain a sealed interface between shaft 108 and O-rings 122, 123 preventing a flow of fluid and extraneous materials into shaft cavity 118.

Embodiments of valve 102 also include a flexible sheath 128 operable to prevent extraneous materials from entering flow cavity 114 through hole 132 or shaft 108. In one embodiment, flexible sheath 128 is a waterproof flexible material such as latex or plastic. Flexible sheath 128 can be coupled to o-ring 122 extending over the portion of shaft 108 that is exposed in flow cavity 114. Flexible sheath 128 is able to flex and move with shaft 108 as it is rotated or moved into and out of shaft cavity 118 thereby preventing a user or any other item/material from coming in direct contact with shaft 108 and entering shaft cavity 118 or flow cavity 114. In another embodiment, flexible sheath 128 is coupled to o-ring 122 extending and covering the portion of shaft 108 within the flow cavity 114. Again, in this embodiment as well, flexible tube 128 prevents any extraneous items/materials from entering the flow cavity 114. It should be appreciated that embodiments of flexible sheath 128 include flexible sheath 128 being affixed to shaft 108, o-rings 122, 123 or to valve 102 provided that it prevents extraneous materials from entering flow cavity 114.

Embodiments of shaft 108 provide that shaft 108 can be operably separated into two portions within shaft cavity 118 and also reattached. Embodiments of shaft 108 allow a user to (1) move shaft 108 rotationally or longitudinally relative to body 103 within shaft cavity 118 to align pin 120 with a desired groove 116, and (2) detach or remove the portion of shaft 108 that is exposed from shaft cavity 118. Embodiments of shaft 108 operably prevent a patient with valve 102 attached to their ventricles from adjusting the pressure settings of valve 102 themselves.

It should be appreciated that while embodiments of valve 102 have been described in relation to drainage of cerebrospinal fluid from a user's ventricles, embodiments of valve 102 are applicable in many other areas that require pressure regulated drainage of bodily fluids. For instance, embodiments of valve 102 can be used in a peritoneovenous shunt (also known as Denver Shunt) in the drainage of peritoneal fluid from the peritoneum into veins. Valve 102 can generally be used in drainage of bodily fluids from a wound, in non-acute controlled wound drainage, lumbar spinal drainage (e.g., lumbar-peritoneal shunts that drain excess cerebrospinal fluid from the subarachnoid cavity). Embodiments of valve 102 can further be used in the controlled delivery of fluid to a user rather than drainage. For instance, valve 102 is operable for delivering biomedical fluids and microfluidics to a user intravenously.

Figure 2:
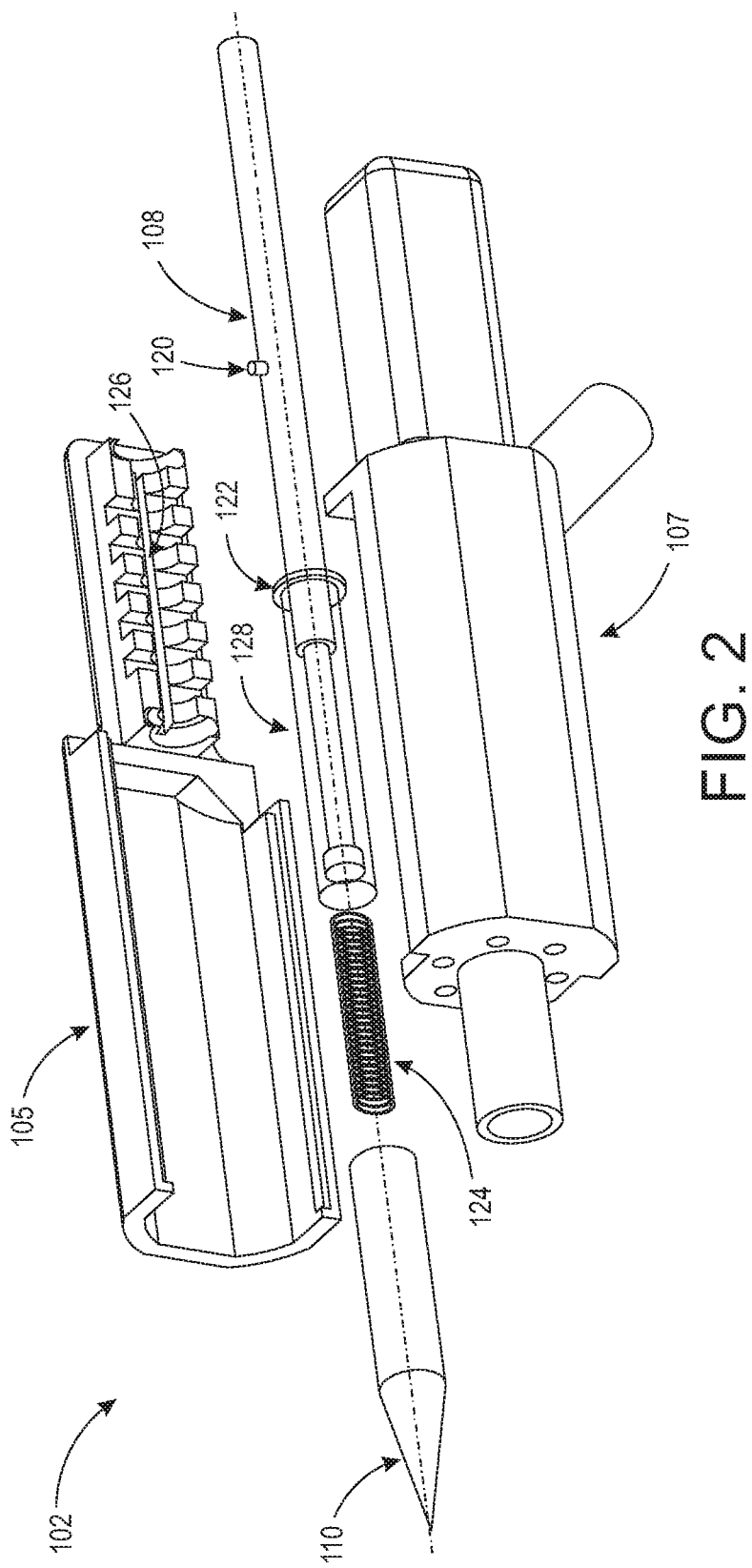
FIG. 2 is an exploded view of a valve suitable for use in practicing exemplary embodiments of this disclosure.

Referring to FIG. 2, shown is an exploded view of the valve 102 suitable for use in practicing exemplary embodiments of this disclosure. Illustrated in FIG. 2 is valve 102 having a first body portion 105, a second body portion 107, shaft 108, spring 124, and needle head 110. Embodiments of valve 102 provide that body 103 be separated into first body portion 105 and second body portion 107 to provide easier assembly. Embodiments of first body portion 105 and second body portion 107 provide a sealed interface when attached to one another along their periphery to prevent the leakage fluid from flow cavity 114 and to keep out extraneous materials.

Figure 3:
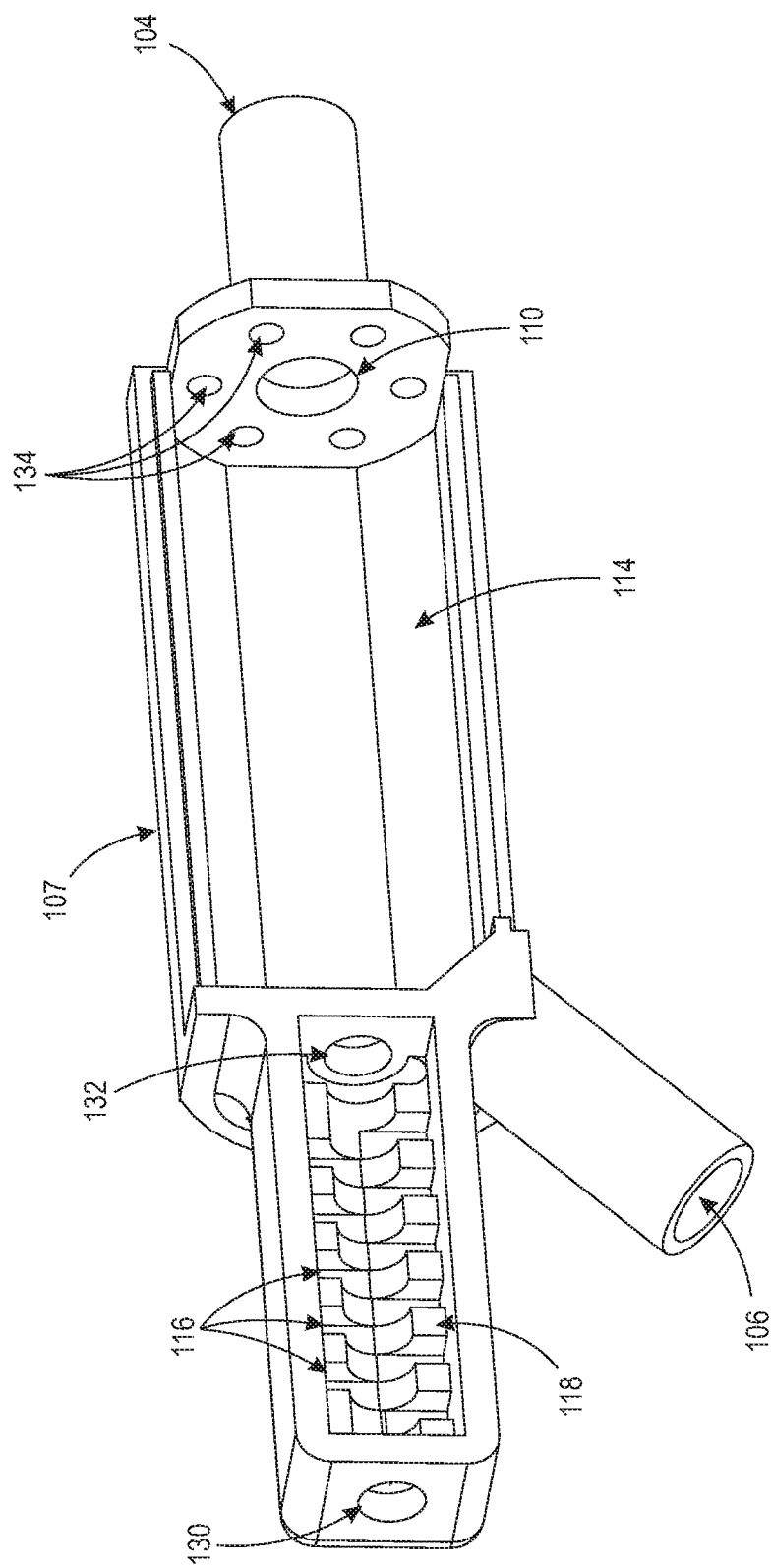
FIG. 3 is a close-up view of a portion of a valve suitable for use in practicing exemplary embodiments of this disclosure.

Reference is now made to FIG. 3, which depicts a close-up view of a portion of the valve suitable for use in practicing exemplary embodiments of this disclosure. Shown in FIG. 3 is valve body 107 having inlet port 104, outlet port 106, flow cavity 114, shaft cavity 118, grooves 116, hole 130, hole 132, and vents 134.

Vents 134 provide a passage into flow cavity 114 allowing air to enter and exit flow cavity 114, but preventing the passage of liquids through vents 134. Embodiments of vents 134 provide a means of establishing and maintaining atmospheric pressure on an interior of flow cavity 114 thereby aiding in a desired flow of fluid (i.e., CSF) through valve 102. Vents 134 can be sealed with a membrane such that (i) air can pass freely into and out of flow cavity 114 through vents 134 and (ii) liquids cannot flow into and out of flow cavity 114. An exemplary membrane includes a hydrophobic membrane placed over vents 134.

Figure 4:
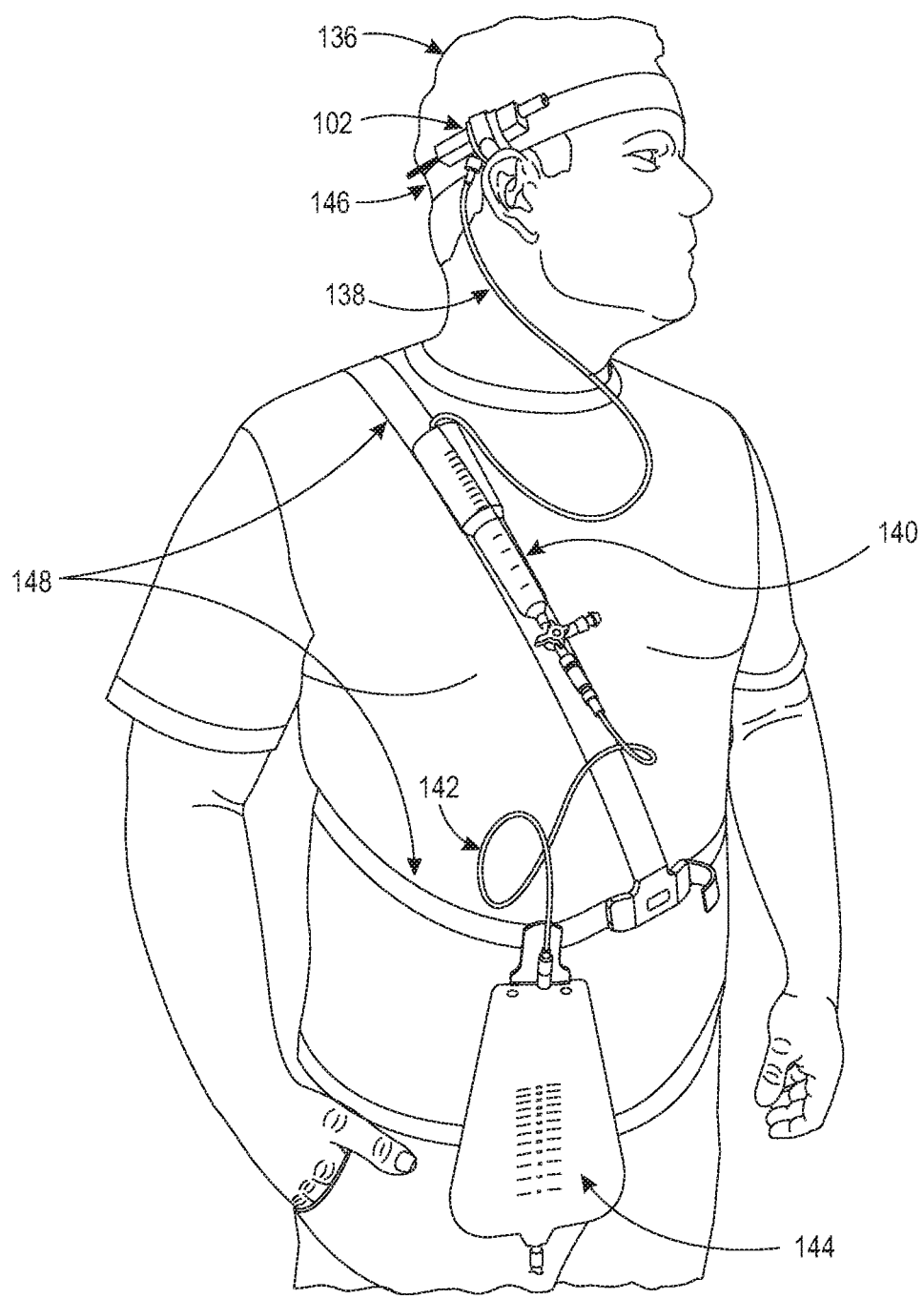
FIG. 4 is a valve system suitable for use in practicing exemplary embodiments of this disclosure.

Reference is now made to FIG. 4, which illustrates an exemplary EVD suitable for use in practicing exemplary embodiments of this disclosure. Shown in FIG. 4 are valve 102, catheter 136, tube 138, graduated cylinder 140, tube 142, drainage bag 144, and user strap 146. Catheter 136 is operably connected to the ventricles of the user to allow for flow of CSF. Valve 102 is fluidly connected to catheter 136 to receive a flow of CSF from catheter 136. Valve 102 is removeably coupled to head strap 146. Head strap 146 is operable to be removeably attached to a user's head. Embodiments of head strap 146 are adjustable to fit the size and shape of a user's head. Valve 102 is located on the user's head at the same level of the user's ventricles.

Tube 138 is fluidly connected to outlet port 106 of valve 102 allowing a flow of CSF from valve 102 through tube 138. Tube 138 is fluidly connected to graduated cylinder 140 providing a flow of CSF from valve 102. Graduated cylinder 140 includes measurement indicators to allow a user or medical professional to determine a volume of flow of CSF from the user's ventricles. It should be appreciated that embodiments of graduated cylinder 140 include any type of fluid measuring device that allows a user or medical professional to determine a volume of flow of CSF from the user's ventricles. Graduated cylinder 140 is operably located at level below valve 102 to allow a flow of CSF from valve 102 based on the natural gravitational pull. Embodiments of graduated cylinder 140 include a stop cock operable to prevent a flow of fluid from graduated cylinder 140 to tube 142 thereby allowing a buildup of fluid within graduated cylinder 140. Graduated cylinder 140 also include at least one atmospheric vent allowing for a passage of air between the interior of graduated cylinder 140 and the outside atmosphere. Graduated cylinder 140 is removeably attached to user strap 148, which is adjustable to fit the size and shape of a user's body.

Tube 142 is fluidly connected to graduated cylinder 140 allowing a flow of CSF fluid from graduated cylinder 140 through tube 142. Tube 142 is also fluidly connected to drainage bag 144. In the embodiment shown in FIG. 4, drainage bag 144 is removeably attached to user strap 148 and is located at a level below graduated cylinder 140. Embodiments of drainage bag 144 are operably located at a level below graduated cylinder 140 to allow a flow of CSF from graduated cylinder 140 based on the natural gravitational pull. It should be appreciated that embodiments of user strap 148 include any type of arrangement including cross body straps, belts, suspenders or a combination of any that allow a user to removeably attach the present system to a user's body as described herein.

Figure 5:
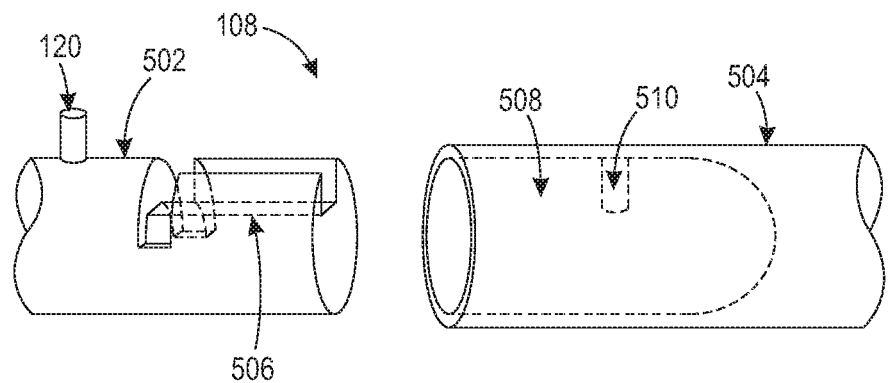
FIG. 5 is a close up view of a shaft suitable for use in practicing exemplary embodiments of this disclosure.

Referring to FIG. 5, shown is a close up view of a shaft 108 suitable for use in practicing exemplary embodiments of this disclosure. Shown in FIG. 5 is shaft 108 with shaft cavity portion 502 and shaft user portion 504. Shaft cavity portion 502 operably is within shaft cavity 118 and includes pin 120 for selectively locating within grooves 116. Shaft cavity portion 502 also includes recess 506, which is located on the radial surface of shaft cavity portion 502. As shown in FIG. 5, recess 506 is in a "T" shape and is sized to correspond and interact with shaft user portion 504. It should be appreciated that embodiments of recess 506 can include multiple shapes provided that it allows shaft cavity portion 502 and shaft user portion 504 to both be removeably attached and to move relative to body 103 as desired by a user.

Shaft user portion 504 includes cavity 508 extending within the long axis of shaft user portion 504. Cavity 508 is sized to encompass and correspond to the distal end of shaft cavity portion 502. Cavity 508 includes a pin 510, which extends radially inward from an interior surface of shaft user portion 504 within cavity 508. Pin 510 is sized to correspond and interact with recess 506 such that shaft user portion 504 can be selectively attached to and detached from shaft cavity portion 502 allowing a user to both rotate shaft 108 (including shaft cavity portion 502) around its long axis and to also move shaft 108 (including shaft cavity portion 502) longitudinally toward and away from inlet port 104.

Figure 6:
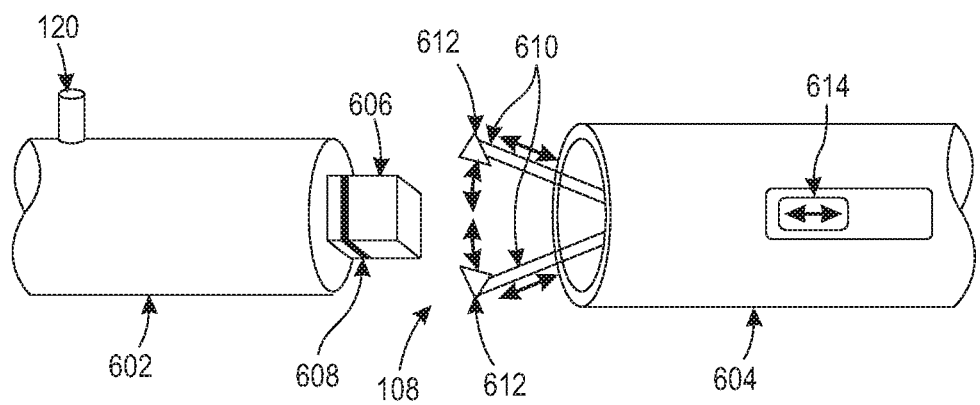
FIG. 6 is a close up view of an alternative shaft suitable for use in practicing exemplary embodiments of this disclosure.

Referring to FIG. 6, shown is a close up view of an alternative shaft 108 suitable for use in practicing exemplary embodiments of this disclosure. Shown in FIG. 6 is shaft 108. Shaft 108 includes a shaft cavity portion 602 and shaft user portion 604. Shaft cavity portion 602 includes pin 120 and distal cube 606. Distal cube 606 extends along the long axis of shaft cavity portion 602 from the distal end of shaft cavity portion 602. Distal cube 606 includes a notch 608 which surrounds circumferentially distal cube 606. Notch 608 presents a raised portion for interaction with shaft user portion 604. It should be appreciated that embodiments of distal cube 606 include multiple shapes (e.g., circular, polygon) that would allow for attachment to shaft user portion 604.

Shaft user portion 604 includes attachment tongs 610, which extend along the long axis of shaft user portion 604 from the end of shaft user portion 604. Embodiments of tongs 610 include 2 or more arms with one or more catches 612 for removeably attaching to notch 608. Tongs 610 can operably move in multiple directions. First, tongs 610 can move along the long axis shaft user portion 604 by both extending to and from shaft user portion 604. Second, tongs 610 can move toward and away from the radial center of the long axis of shaft user portion 604.

Tongs 610 are operable to removeably attach shaft user portion 604 to shaft cavity portion 602 by removeably attaching catches 612 of tongs 610 to notch 608 on distal cube 608. Movement of tongs 610 can be controlled by switch 614. Switch 614 is operably moveable along the long axis of shaft user portion 604 allowing the user to selectively move switch 614 and thus tongs 610 to multiple locations. It should be appreciated that embodiments of switch 614 include any type of mechanism that allows a user to selectively control movement of tongs 610.

In practice, shaft 108 can be advanced toward needle seat 112 in order to compress spring 124 and bias needle head 110 toward needle seat 112. Embodiments of shaft 108 may be cylindrical, or may have a plunger and recess machined into the diameter of shaft 108. The recess allows for angular shifting of needle head 110 in order to ensure proper seating of needle head 110. The recess also allows any water that gets inside the needle to have a path to exit the needle, thus eliminating the possibility of water exerting a force between shaft 108 and needle head 110 altering the applied cracking pressure. The alignment of needle head 110 to needle seat 112 is highly critical. Improper alignment of needle head 110 to needle seat 112 will lead to improper flow through valve 102. Also, shaft 108 should be properly sized to allow needle head 110 to move with little to no friction.

Figure 7:
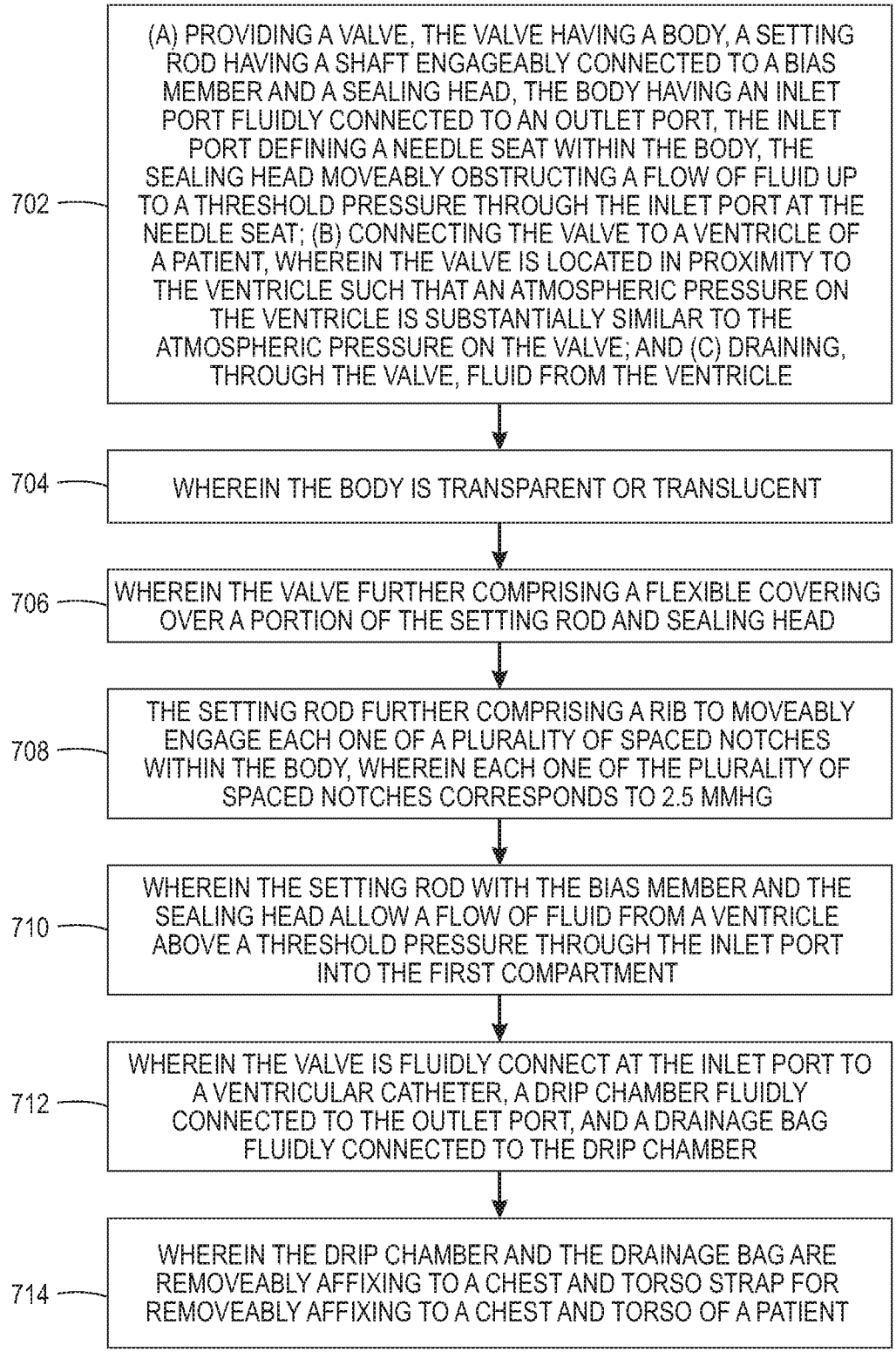
FIG. 7 is a logic flow diagram in accordance with a method and apparatus for performing exemplary embodiments of this disclosure.

FIG. 7 presents a summary of the above teachings for draining. Block 702 presents (a) providing a valve, the valve having a body, a setting rod having a shaft engageably connected to a bias member and a sealing head, the body having an inlet port fluidly connected to an outlet port, the inlet port defining a needle seat within the body, the sealing head moveably obstructing a flow of fluid up to a threshold pressure through the inlet port at the needle seat; (b) connecting the valve to a ventricle of a patient, wherein the valve is located in proximity to the ventricle such that an atmospheric pressure on the ventricle is substantially similar to the atmospheric pressure on the valve; and (c) draining, through the valve, fluid from the ventricle. Then block 704 specifies wherein the body is transparent or translucent.

Some of the non-limiting implementations detailed above are also summarized at FIG. 7 following block 704. Block 706 relates to wherein the valve further comprising a flexible covering over a portion of the setting rod and sealing head. Block 708 further specifies the setting rod further comprising a rib to moveably engage each one of a plurality of spaced notches within the body, wherein each one of the plurality of spaced notches corresponds to 2.5 mmHg. Block 710 then states wherein the setting rod with the bias member and the sealing head allow a flow of fluid from a ventricle above a threshold pressure through the inlet port into the first compartment. Block 712 then relates to wherein the valve is fluidly connect at the inlet port to a ventricular catheter, a drip chamber fluidly connected to the outlet port, and a drainage bag fluidly connected to the drip chamber. Block 714 then specifies wherein the drip chamber and the drainage bag are removeably affixing to a chest and torso strap for removeably affixing to a chest and torso of a patient.

The invention has been described in detail with particular reference to a presently preferred embodiment, but it will be understood that variations and modifications can be effected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for draining, the apparatus comprising:
   (a) a body, the body having a first compartment adjacent to a second compartment, the first compartment having an inlet port fluidly connected to an outlet port, the inlet port defining a needle seat within the first compartment, a first rod hole for operation with a second rod hole in the second compartment, and a plurality of venting holes, the second compartment having a plurality of spaced notches along;
   (b) a setting rod, the setting rod having a shaft and a sealing head, the shaft sized to be slideably maintained in the first rod hole and the second rod hole, the sealing head slideably attached to an end of the shaft and sized to obstruct fluid flow from the inlet port at the needle seat; and
   (c) a bias member, the bias member intermediate the setting rod and the sealing head for exerting a force on the sealing head against the needle seat.

2. The apparatus according to claim 1, wherein the body is transparent or translucent.

3. The apparatus according to claim 1, further comprising a flexible covering over the shaft and sealing head contained in the first compartment.

4. The apparatus according to claim 1, the setting rod further comprising a rib sized to engage each one of the plurality of spaced notches, wherein each one of the plurality of spaced notches corresponds to 2.5 mmHg acting on the sealing head.

5. The apparatus according to claim 1, comprising two O-rings circumscribing the shaft located in the second compartment at the first rod hole and the second rod hole to allow the shaft to slideably move through the first rod hole and the second rod hole.

6. The apparatus according to claim 1, wherein the setting rod with the bias member and the sealing head substantially prevent a flow of fluid from a ventricle up to a threshold pressure through the inlet port.

7. The apparatus according to claim 1, wherein the setting rod with the bias member and the sealing head allow a flow of fluid from a ventricle above a threshold pressure through the inlet port into the first compartment.

8. The apparatus according to claim 7, wherein the outlet port allows a flow of fluid to exit the first compartment.

9. The apparatus according to claim 1, further comprising a ventricle catheter fluidly connected to the inlet port, a drip chamber fluidly connected to the outlet port, and a drainage bag fluidly connected to the drip chamber.

10. The apparatus according to claim 9, further comprising a chest and torso strap coupled to the drip chamber and the drainage bag for removeably affixing the drip chamber and the drainage bag to a chest and torso of a patient.

11. A method for draining, the method comprising:
    (a) providing a valve, the valve having a body, the body having a first compartment adjacent to a second compartment, the first compartment having an inlet port fluidly connected to an outlet port, the inlet port defining a needle seat within the first compartment, a setting rod having a shaft engageably connected to a bias member and a sealing head, a first rod hole for operation with a second rod hole in the second compartment, the shaft sized to be slideably maintained in the first rod hole and the second rod hole and a plurality of venting holes, the second compartment having a plurality of spaced notches along, the sealing head moveably obstructing a flow of fluid up to a threshold pressure through the inlet port at the needle seat;
    (b) connecting the valve to a ventricle of a patient, wherein the valve is located in proximity to the ventricle such that an atmospheric pressure on the ventricle is substantially similar to the atmospheric pressure on the valve; and
    (c) draining, through the valve, fluid from the ventricle.

12. The method according to claim 11, wherein the body is transparent or translucent.

13. The method according to claim 11, wherein the valve further comprising a flexible covering over a portion of the setting rod and sealing head.

14. The method according to claim 11, the setting rod further comprising a rib to moveably engage each one of a plurality of spaced notches within the body, wherein each one of the plurality of spaced notches corresponds to 2.5 mmHg.

15. The method according to claim 11, wherein the setting rod with the bias member and the sealing head allow a flow of fluid from a ventricle above a threshold pressure through the inlet port into the first compartment.

16. The method according to claim 11, wherein the valve is fluidly connect at the inlet port to a ventricle catheter, a drip chamber fluidly connected to the outlet port, and a drainage bag fluidly connected to the drip chamber.

17. The method according to claim 11, wherein the drip chamber and the drainage bag are removeably affixing to a chest and torso strap for removeably affixing to a chest and torso of a patient.

* * * * *